(12) United States Patent
Song et al.

(10) Patent No.: US 11,717,271 B2
(45) Date of Patent: Aug. 8, 2023

(54) THERMALLY-CONDUCTIVE MATERIAL LAYER AND INTERNAL STRUCTURE FOR ULTRASOUND IMAGING

(71) Applicant: KONINKLIJKE PHILIPS N.V., Eindhoven (NL)

(72) Inventors: Junho Song, N. Andover, MA (US); Edward Chan, Brookline, MA (US); Steven Michael Tavoletti, Reading, MA (US); Mehdi Hejazi Dehaghani, Salem, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 92 days.

(21) Appl. No.: 17/043,692

(22) PCT Filed: Mar. 22, 2019

(86) PCT No.: PCT/EP2019/057249
§ 371 (c)(1),
(2) Date: Sep. 30, 2020

(87) PCT Pub. No.: WO2019/185478
PCT Pub. Date: Oct. 3, 2019

(65) Prior Publication Data
US 2021/0059645 A1    Mar. 4, 2021

Related U.S. Application Data
(60) Provisional application No. 62/650,799, filed on Mar. 30, 2018.

(51) Int. Cl.
*A61B 8/00* (2006.01)
(52) U.S. Cl.
CPC ............ *A61B 8/546* (2013.01); *A61B 8/4236* (2013.01); *A61B 8/4254* (2013.01); *A61B 8/4455* (2013.01); *A61B 8/4494* (2013.01)

(58) Field of Classification Search
CPC ..... A61B 8/546; A61B 8/4455; A61B 8/4494; A61B 8/4444
See application file for complete search history.

(56) References Cited

U.S. PATENT DOCUMENTS

| | | | |
|---|---|---|---|
| 5,213,103 A | 5/1993 | Martin et al. | |
| 5,545,942 A | 8/1996 | Jaster et al. | |

(Continued)

FOREIGN PATENT DOCUMENTS

| | | |
|---|---|---|
| JP | H10126887 A | 5/1998 |
| WO | 2016125040 A2 | 8/2016 |

OTHER PUBLICATIONS

R. Roth, T. Watanabe, T. Kobayashi and K. Hirano, "Thermal resistance of ultrasound probe cable," 2017 IEEE International Ultrasonics Symposium (IUS), 2017, pp. 1-3, doi: 10.1109/ULTSYM.2017.8091733.; also available at https://ieeexplore.ieee.org/stamp/stamp.jsp?tp=&arnumber=8091733 (Year: 2017).*

(Continued)

*Primary Examiner* — Christopher L Cook

(57) ABSTRACT

An ultrasound imaging probe including a handle configured for handheld use; a support structure disposed within the handle and comprising a thermally-conductive material, the support structure further comprising a coupling surface and an external surface, the coupling surface disposed at a distal portion of the support structure; a continuous material layer coupled to the support structure, such that the continuous material layer is disposed on the coupling surface and the external surface, the continuous material layer thereby providing a heat transmission path between the coupling surface and the external surface; and an ultrasound sensor coupled to the support structure at the coupling surface and directly in contact with the continuous material layer at the coupling surface, such that heat from the ultrasound sensor is trans- (Continued)

mitted away to the support structure via the heat transmission path of the continuous material layer.

15 Claims, 11 Drawing Sheets

(56) References Cited

U.S. PATENT DOCUMENTS

| | | | |
|---|---|---|---|
| 5,721,463 A | 2/1998 | Snyder | |
| 7,314,447 B2 | 1/2008 | Park et al. | |
| 2006/0261707 A1 | 11/2006 | Wildes et al. | |
| 2008/0188755 A1* | 8/2008 | Hart | A61B 8/00 |
| | | | 600/459 |
| 2009/0062656 A1* | 3/2009 | Hyuga | A61B 8/445 |
| | | | 600/459 |
| 2013/0301395 A1* | 11/2013 | Hebrard | A61B 8/546 |
| | | | 367/189 |
| 2013/0303918 A1* | 11/2013 | Miyajima | A61B 8/4444 |
| | | | 600/459 |
| 2014/0050915 A1* | 2/2014 | Min | C09J 7/38 |
| | | | 428/323 |
| 2014/0058270 A1* | 2/2014 | Davidsen | A61B 8/4494 |
| | | | 600/459 |
| 2014/0364742 A1* | 12/2014 | Cho | A61B 8/4444 |
| | | | 600/459 |
| 2015/0065883 A1 | 3/2015 | Lee et al. | |
| 2015/0289851 A1 | 10/2015 | Kobayashi et al. | |
| 2016/0174939 A1* | 6/2016 | Cho | B06B 1/0629 |
| | | | 600/459 |
| 2017/0164926 A1 | 6/2017 | Spicci et al. | |
| 2019/0162832 A1* | 5/2019 | Otsuka | F28D 15/0275 |

OTHER PUBLICATIONS

Motoki et al: "Optimized Backing Design for a 3D Transthoracic Echocardiography (TTE) Probe"; 2016 IEEE International Ultrasonics Symposium Proceedings, pp. 1-3.
PCT/EP2019/057249 ISR & Written Opinion, dated May 29, 2019, 14 Page Document.

* cited by examiner

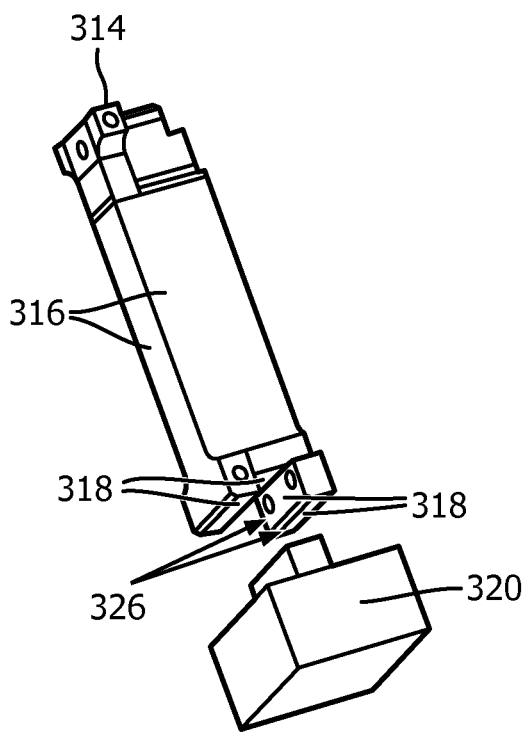
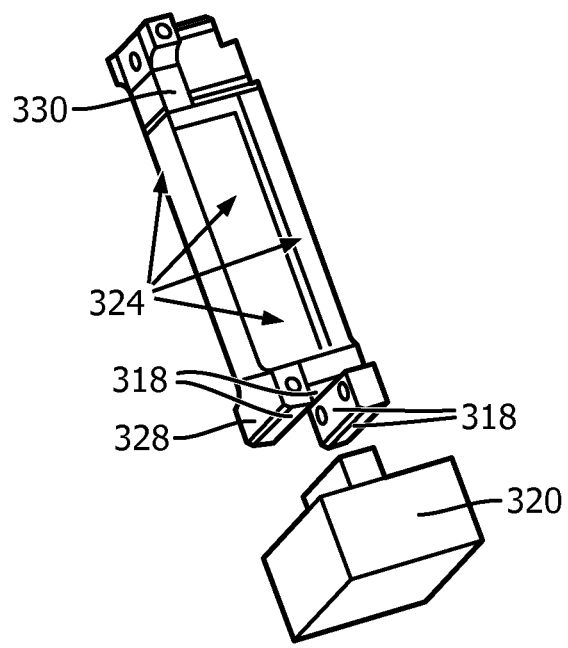
FIG. 3A
FIG. 3B
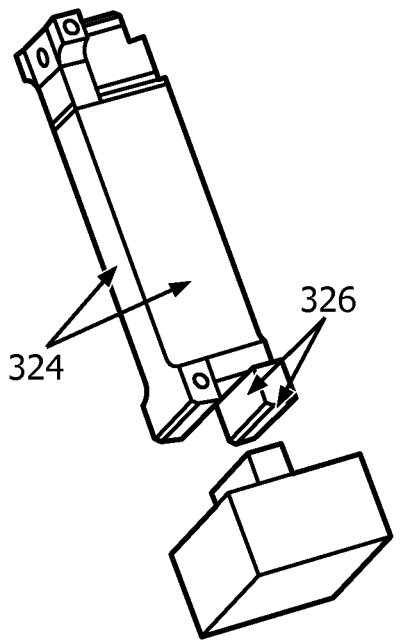
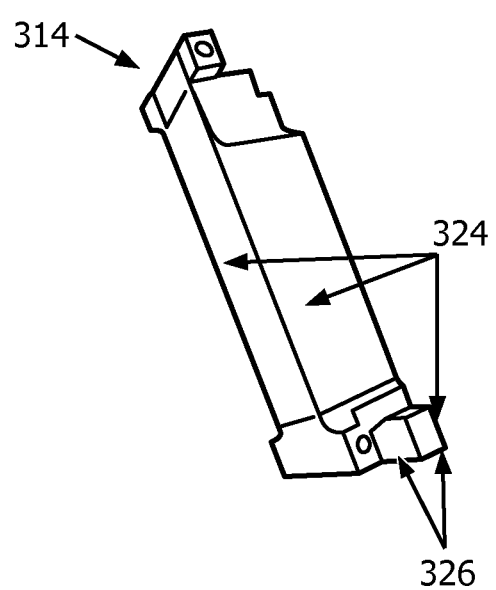
FIG. 3C
FIG. 3D

THERMALLY-CONDUCTIVE MATERIAL LAYER AND INTERNAL STRUCTURE FOR ULTRASOUND IMAGING

CROSS-REFERENCE TO PRIOR APPLICATIONS

This application is the U.S. National Phase application under 35 U.S.C. § 371 of International Application No. PCT/EP2019/057249, filed on Mar. 22, 2019, which claims the benefit of U.S. Provisional Patent Application No. 62/650,779, filed on Mar. 30, 2018. These applications are hereby incorporated by reference herein.

TECHNICAL FIELD

The present disclosure relates generally to an ultrasound imaging probe, and in particular, to enhancing an ultrasound imaging probe's thermal dissipation capabilities by disposing an internal structure of the probe with a thermally-conductive material layer.

BACKGROUND

Medical ultrasound sensors or transducers use high frequency sound waves to produce images of internal organs, vessels, and tissues. In general, the higher the acoustic power of the ultrasound sensor, the better the image quality. Thus, it is often desirable to operate a medical ultrasound sensor at a high acoustic power to achieve high image quality in medical imaging. However, operating a sensor at high power also generates a high amount of heat at an acoustic stack or transducer assembly. Such high heat may cause the surface temperature of the transducer to exceed a regulated temperature limit.

Traditionally, heat spreaders are commonly applied underneath the acoustic stack to help dissipate the heat produced by the transducer. However, traditional heat spreader designs have been unable to keep up with the high power and temperature demands of modern ultrasound transducers. As a result, doctors and ultrasound technicians have been forced to reduce acoustic power at the expense of image quality. Some alternatives, such as actively cooled sensor assemblies, are complicated and expensive.

SUMMARY

Physicians require high ultrasound power inputs to produce higher resolution ultrasound images. However, such high power inputs produce high amounts of heat. By wrapping the internal components of an ultrasound imaging probe with a highly-conductive material layer, such as graphite, the present invention allows an ultrasound probe to dissipate heat much more quickly than a conventional ultrasound probe. As a result, a physician using an ultrasound probe wrapped with the thermally conductive material may continue high-resolution imaging at full power for extended periods of time. By contrast, conventional ultrasound probes equipped with traditional heat spreaders may need to have their imaging power and imaging resolution reduced, or even be powered down, to keep within temperature limits. Thus, according to aspects of the present disclosure, traditional heat spreaders may advantageously be replaced with simple, cheap, and thermally-effective conductive material layer designs.

Specifically, a thermally conductive material layer may be applied to the coupling surfaces of the internal support structure which are in contact with the ultrasound sensor. The material layer facilitates the transfer and dissipation of heat from the heat-generating components of the ultrasound imaging probe, such as the ultrasound sensor, to the non-heat generating components of the ultrasound imaging probe, such as the support structure. To further enhance thermal dissipation, the material layer may also be applied to the external surfaces of the support structure, the ferrule, and the communications elements (cables, wires, optic fibers, etc.). Wrapping the internal support structure with graphite has in some examples resulted in a temperature reduction of 8 degrees Celsius compared to traditional materials and designs.

In one embodiment, an ultrasound imaging probe includes a handle configured for handheld use; a support structure disposed within the handle and comprising a thermally-conductive material, the support structure further comprising a coupling surface and an external surface, the coupling surface disposed at a distal portion of the support structure; a continuous material layer coupled to the support structure, such that the continuous material layer is disposed on the coupling surface and the external surface, the continuous material layer thereby providing a heat transmission path between the coupling surface and the external surface; and an ultrasound sensor coupled to the support structure at the coupling surface and directly in contact with the continuous material layer at the coupling surface, such that heat from the ultrasound sensor is transmitted away to the support structure via the heat transmission path of the continuous material layer.

In some embodiments, the coupling surface of the ultrasound imaging probe is a planar surface and the external surface each comprises a planar surface of the support structure. In some embodiments, the ultrasound sensor includes an acoustic stack and an acoustic backing material adjacent to the acoustic stack, wherein a surface of the ultrasound sensor that is directly in contact with the continuous material layer includes a surface of the acoustic backing material. In some embodiments, the ultrasound sensor includes an acoustic stack, an acoustic backing material adjacent to the acoustic stack, and a heat-conductive structure adjacent to the backing material, wherein a surface of the ultrasound sensor that is directly in contact with the continuous material layer includes a surface of the heat-conductive structure. In some embodiments, a material layer is disposed on an external surface of the ultrasound sensor, and a surface of the ultrasound sensor that is directly in contact with the continuous material layer includes a surface of the disposed material layer. In some embodiments, the support structure includes a body and a protrusion extending from the body at the distal portion, wherein a surface of the protrusion comprises the coupling surface and a surface of the body comprises the external surface. In some embodiments, the external surface extends along a longitudinal axis of the support structure. In some embodiments, the continuous material layer comprises a graphite sheet bonded to an adhesive. In some embodiments, the ultrasound imaging probe further includes a second continuous material layer disposed on one or more external surfaces of the ultrasound sensor and the support structure, such that the second continuous material layer provides a second heat transmission path from the one or more external surfaces of the ultrasound sensor to the one or more external surfaces of the support structure, thereby also transmitting the heat away to the support structure. In some embodiments, the ultrasound imaging probe further includes a ferrule and a second continuous material layer disposed on one or more external surfaces of the ultrasound sensor, the support structure, and the ferrule, such that the second continuous material layer provides a second heat transmission path from the one or more external surfaces of the ultrasound sensor to the one or more external surfaces of the support structure and the ferrule, thereby also transmitting the heat away to the support structure and the ferrule.

In one embodiment, an ultrasound imaging probe includes a handle configured for handheld use; a support structure disposed within the handle and comprising a thermally-conductive material, the support structure further comprising a ferrule, wherein the ferrule is disposed at a proximal portion of the support structure; an ultrasound sensor coupled to a distal portion of the support structure; and a continuous material layer disposed on external surfaces of the ultrasound sensor, the support structure, and the ferrule, the continuous material layer thereby providing a heat transmission path from the ultrasound sensor to the support structure and the ferrule, wherein the ultrasound sensor is directly in contact with the continuous material layer disposed on the external surfaces of the ultrasound sensor, such that heat from the ultrasound sensor is transmitted away to the support structure and the ferrule via the heat transmission path of the continuous material layer.

In some embodiments, the ultrasound imaging probe further includes a communication cable disposed within the ferrule and in direct contact with an internal surface of the ferrule. In some embodiments, the communication cable is thermally coupled to the ferrule such that the heat is also transmitted away from ultrasound sensor to the communication cable via the heat transmission path of the continuous material layer. In some embodiments, the ultrasound sensor includes an acoustic stack and an acoustic backing material adjacent to the acoustic stack, wherein a surface of the ultrasound sensor that is directly in contact with the continuous material layer includes a surface of the acoustic backing material. In some embodiments, the ultrasound sensor includes an acoustic stack, an acoustic backing material adjacent to the acoustic stack, and a heat-conductive structure adjacent to the backing material, wherein a surface of the ultrasound sensor that is directly in contact with the continuous material layer includes a surface of the heat-conductive structure. In some embodiments, the external surface extends along a longitudinal axis of the support structure. In some embodiments, the continuous material layer includes a graphite sheet bonded to an adhesive. In some embodiments, the support structure includes a body, and wherein the ferrule is coupled to the body at a proximal portion of the support structure. In some embodiments, the ultrasound imaging probe further includes a second continuous material layer disposed on a coupling surface and an external surface of the support structure, the ultrasound sensor coupled to the support structure at the coupling surface and directly in contact with the second continuous material layer, such that the second continuous material layer provides a second heat transmission path between the coupling surface and the external surface, thereby also transmitting the heat away to the support structure.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 3A is an exemplary illustration of a support structure in relation to a material layer disposed on various surfaces of the support structure, according to aspects of the present disclosure.

FIG. 3B is another exemplary illustration of a support structure in relation to a material layer disposed on various surfaces of the support structure, according to aspects of the present disclosure.

FIG. 3C is a further exemplary illustration of a support structure in relation to a material layer disposed on various surfaces of the support structure, according to aspects of the present disclosure.

FIG. 3D is an exemplary photograph of a support structure in relation to a material layer disposed on various surfaces of the support structure, according to aspects of the present disclosure.

DETAILED DESCRIPTION

Figure 1:
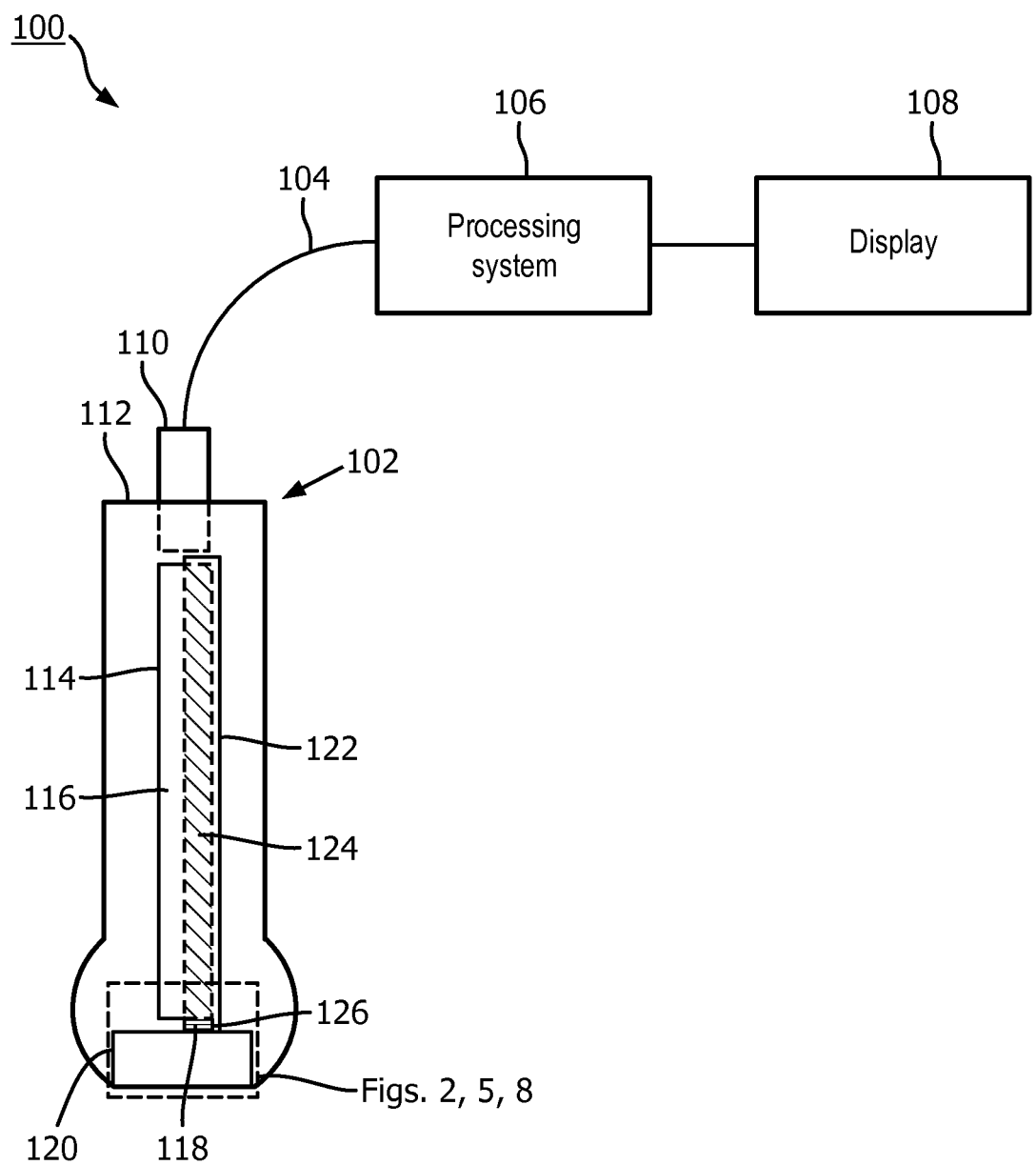
FIG. 1 is a diagrammatic schematic view of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100, according to aspects of the present disclosure. The ultrasound imaging system 100 may include an ultrasound imaging probe 102, a processing system 106, and a display 108. In some circumstances, the system 100 may include additional elements and/or may be implemented without one or more of the elements illustrated in FIG. 1.

It is understood that the system 100 and/or probe 102 can be configured to obtain any suitable ultrasound imaging data. In some embodiments, the imaging probe 102 is sized and shaped to be placed on or near the anatomy of the subject to perform an ultrasound imaging procedure. The imaging probe 102 may be placed directly on the body of the subject and/or adjacent the body of the subject. For example, the imaging probe 102 may be directly in contact with the body of the subject while obtaining imaging data. In some embodiments, the probe 102 includes one or more imaging elements which may be placed directly on or adjacent the body of the subject. In other embodiments, a housing of the imaging probe is placed directly in contact with the body of the subject such that the imaging elements are adjacent the body of the subject. The subject may be a human patient or animal. The imaging probe 102 may be portable and may be suitable to be used by a user in a medical setting. For example, the imaging probe 102 may be a Doppler ultrasound imaging probe.

Generally, the imaging probe 102 may be configured to emit ultrasonic energy in order to create an image of a surrounding anatomy within the body of a patient. For example, the imaging probe 102 may be positioned proximate to and/or in contact with the body of the patient over the anatomy of interest. The operator of the imaging probe 102 may contact a distal portion of the imaging probe to the body of the patient such that the anatomy is compressed in a resilient manner. The view of the anatomy shown in the ultrasound image depends on the position and orientation of the imaging probe 102. To obtain imaging data of the vessel or lumen, the imaging probe 102 can be suitably positioned either manually by a clinician and/or automatically by the operator so that the ultrasound sensor 120 emits ultrasound waves and receives ultrasound echoes from the appropriate portion of the anatomy. The ultrasound sensor 120 can be referenced as a transducer or a transducer array in some instances.

The ultrasonic waves emitted by the ultrasound sensor 120 of the probe 102 may be reflected by discontinuities arising from tissue structures within the patient body, and other features of interest. Generally, the probe 102 can be utilized to visualize any suitable anatomy and/or body lumen of the patient. Echoes from the reflected waves are received by the imaging probe 102 and passed along to the processing system 106. The processing system 106 processes the received ultrasound echoes to produce an image of the anatomy of the patient based on the acoustic impedance associated with the ultrasound echoes. The processing system 106 may be configured to generate a B-mode (brightness mode) imaging of anatomy corresponding to the varying acoustic impedance of the received ultrasound echoes. The image may be a two-dimensional cross-sectional image or a three-dimensional image of the anatomy. The imaging probe 102 and/or the processing system 106 may include features similar or identical to those found in commercially available ultrasound imaging elements such as the Lumify probe and system, EPIQ, Affiniti, and/or CX50 ultrasound systems, each available from Koninklijke Philips N. V. Imaging data obtained by the imaging probe 102 can also include velocity data of fluid within the patient body, including Doppler flow and vector flow. The processing system 106 outputs image data such that an image of the vessel or lumen, such as a cross-sectional image of the anatomy, is displayed on the display 108.

The system 100 may be deployed in a medical room where a patient is located. For example, the processing system 106 may be located within the medical room itself or in a room remote from the patient. In some embodiments, probe 102 may be controlled from a remote location, such than an operator is not required to be in close proximity to the patient. The imaging probe 102 and display 108 may be communicatively coupled directly or indirectly to the processing system 106. These elements may be communicatively coupled to the processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or any other high-speed wireless networking standard. In such cases, the elements may include one or more wireless transmission devices, such as antennae and/or transceivers. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

For wired connections, the imaging probe 102 and display 108 may be communicatively coupled using communication cable 104. In such cases, the communication cable 104 may be of a suitable material (e.g., copper, glass fibers, etc.) and type (e.g. USB, Ethernet, etc.) to facilitate communication using the specified communication protocol. The communication cable 104 may also include a power cable to carry power from the processing system 106 to the imaging probe 102. At the junction where the communication cable is coupled to the imaging probe 102, a ferrule 110 may be provided to protect the communication cable from damage by mechanical stresses.

The imaging probe 102 may include a housing 112, a support structure 114, and an ultrasound sensor 120. The housing 112 may surround and protect the various components of the imaging probe 102, and may include a handle for use by an operator. In some embodiments, the housing 112 is portable and may be sized and shaped for handheld grasping by an operator. The housing 112 may be suitable for sterilization processes, and may be water-resistant when closed. The housing 112 may be made up of two parts forming a receptacle for receiving the ultrasound sensor 120, the support structure 114, and the ferrule 110. The housing 112 may also be made up of a single piece molded over the ultrasound sensor 120, the support structure 614, and the ferrule 610. The housing 112 may also be comprised of multiple pieces, which may include complementary mating surfaces or features such as screw holes to facilitate closure. The multiple pieces of the housing 112 may additionally or alternatively be sealed using adhesives.

The support structure 114, which has an external surface 116 and a coupling surface 118, supports the various internal components of the imaging probe 102. For example, the ultrasound sensor 120 may be disposed within a compartment on a distal portion of the housing 112, and may also be coupled temporarily or permanently to the support structure 114 by any coupling technique, including by adhesives, magnets, clamps, screws, nails, rivets, welds, ties, wraps, etc. Similarly, the support structure may be coupled to the ferrule 110 by any technique.

The external surface 116 and coupling surface 118 of the support structure 114 may be of any shape or form, including planar, rectilinear, orthogonal, circular, curved, rounded, elliptical, spherical, etc. The coupling surface 118 at which the ultrasound sensor 120 is coupled to the support structure 114 may be further formed into a shape or structure complementary to that of the ultrasound sensor 120. Thus, the coupling surface 118 may be a planar surface, a receptacle, a socket, a joint, a pivot, a hinge, a clip, a post, a junction, opposing mating surfaces, teeth, gears, etc.

The support structure 114 may be formed of a thermally conductive material, including unalloyed metals such as silver, copper, gold, aluminum, iron, or zinc, alloyed metals such as silver alloys, copper alloys, gold alloys, aluminum alloys, iron alloys, zinc alloys, and/or non-metals such as allotropes of carbon. The support structure 114 may support a memory, a processor, a printed circuit board, and conductive elements such as flat flexible circuits. Such components may be disposed within separate compartments of the housing 112, and/or be coupled to the support structure by any coupling technique such as by using screws.

The processor of the probe 102 may be configured to transmit signals to other elements probe 102 as well as to external devices, such as the processing system 106 and display 108. The processor may be an application-specific integrated circuit (ASIC), a field-programmable gate array (FPGA), a central processing unit (CPU), a digital signal processor (DSP), another hardware device, a firmware device, or any combination thereof configured to perform the operations described herein with reference to the processor. In some embodiments, the processing system 106 includes a processor that is separate from the processor of the probe 102. Image processing is completed by the processor within the probe 102 alone, by the processor in the processing system 106, or by any combination of these processors.

The processor may be communicatively coupled to a memory. In some embodiments, the memory is a random access memory (RAM). In other embodiments, the memory is a cache memory (e.g., a cache memory of the processor), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some embodiments, the memory may include a non-transitory computer-readable medium. The memory may store instructions. The instructions may include instructions that, when executed by a processor, cause the processor to perform operations described herein with reference to the processor in connection with embodiments of the present disclosure.

The ultrasound sensor 120 may include an acoustic stack including a number of acoustic or transducer elements. The acoustic stack may be formed of multiple layers which are subdivided to form one or more acoustic elements. These acoustic elements may be arranged in a one-dimensional array, 1.x-dimensional array, such as a 1.5-dimensional array, or a two-dimensional array, in some instances. Any number of acoustic elements may be included in the ultrasound sensor 120, for example, 1, 2, 4, 8, 16, 32, 64, 128, 256, 512, etc. The ultrasound sensor 120 can be any suitable configuration, such as phased array including a planar array, a curved array, etc. The ultrasound sensor 120 may include a matrix array including one or more segments of acoustic elements (e.g., one or more rows, one or more columns, and/or one or more orientations) that can be uniformly or independently controlled and activated. The ultrasound sensor 120 may include any suitable transducer type, including a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In some embodiments, the acoustic elements of the ultrasound sensor 120 are configured to emit ultrasound signals and receive ultrasound echo signals corresponding to the emitted ultrasound signals. In that regard, the ultrasound sensor 120 may be configured to obtain one-dimensional, two-dimensional, and/or three-dimensional images of the anatomy of the patient. The ultrasound echo signals may be processed by the processor, stored in the memory, and/or transmitted to the processing system 106 for further processing.

The probe 102 may include a material layer 122. The material layer 122 may be disposed in a contiguous, continuous, and/or uninterrupted manner on the external surface 116 and the coupling surface 118 of the support structure 114 by any mechanical or chemical techniques, including dipping, spraying, painting, coating, flame spraying, electroplating, adhering using adhesives, pasting, bonding, clamping, screwing, nailing, riveting, welding, etc. In some embodiments, the material layer 122 is formed from a single contiguous or continuous material layer. Advantageously, a continuous, unbroken, single layer provides efficient thermal conductivity. In other embodiments, the material layer 122 may be formed of multiple separate sheets or layers that overlap or are joined to one another by any technique, such that the layers form a contiguous or continuous material layer 122. Advantageously, the use of multiple separate sheets or layers may allow more complex shapes to be formed, add reinforcement, reduce wastage, make assembly easier, fine-tune thermal conductivities, etc.

Referring now to FIG. 1, the material layer 122 disposed on the external surface 116 is depicted by a first shaded region 124, while the material layer disposed on the coupling surface 118 is depicted by a second shaded region 126 between the distal end of the material layer 122 and the proximal end of the ultrasound sensor 120. The material layer 122 in the second shaded region 126 provides a heat transmission path between the coupling surface 118 and the external surface 116, such that when the ultrasound sensor 120 is coupled to the support structure 114 at the coupling surface 118 and is in direct contact with the material layer 122 in the second shaded region 126, heat from the ultrasound sensor 120 is transmitted away to the support structure 114 via the heat transmission path provided by the material layer 122.

The material layer 122 may be cut from a graphite layer, such as pyrolytic graphite, and may be provided in a ready-to-apply form with an adhesive on one side and a non-adhesive on the opposing side. To preserve the adhesive, the adhesive side of the material layer 122 may be protected by a non-adhesive backing sheet which may be peeled away before application. Any cutting process may be used to cut the material layer into its final ready-to-apply form, including die cutting, laser cutting, computer numerically controlled (CNC) cutting, hydrocutting, or any other cutting process. Graphite is one exemplary material for the layer 122, and other thermally conductive materials may be used in place of or in addition to graphite in the material layer 122. Such materials include: unalloyed metals such as silver, copper, gold, aluminum, iron, or zinc; alloyed metals such as silver alloys, copper alloys, gold alloys, aluminum alloys, iron alloys, zinc alloys; and/or non-metals such as allotropes of carbon.

Figure 2A:
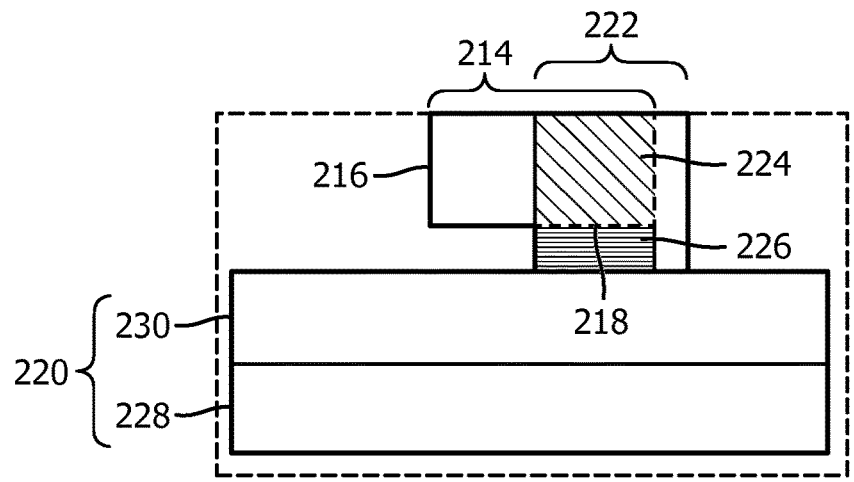
FIG. 2A is an exemplary cross-sectional view of a coupling surface in relation to a support structure, an ultrasound sensor, and a material layer, according to aspects of the present disclosure.
Figure 2B:
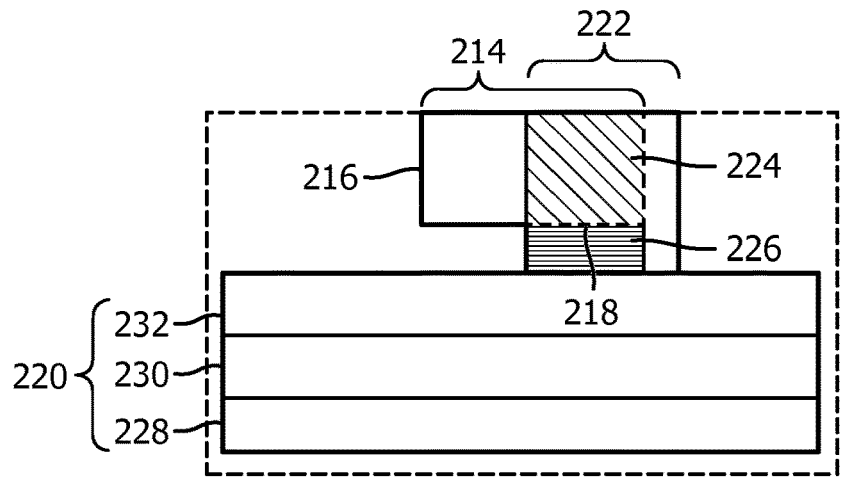
FIG. 2B is another exemplary cross-sectional view of a coupling surface in relation to a support structure, an ultrasound sensor, and a material layer, according to aspects of the present disclosure.
Figure 2C:
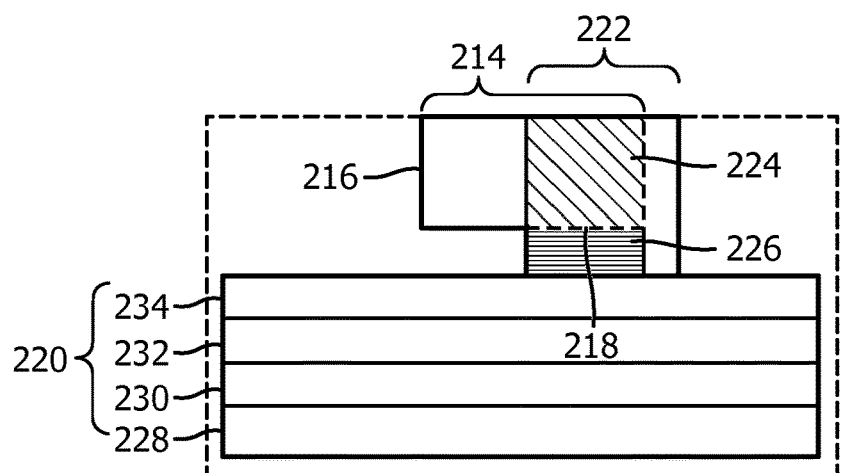
FIG. 2C is a further exemplary cross-sectional view of a coupling surface in relation to a support structure, an ultrasound sensor, and a material layer, according to aspects of the present disclosure.

FIGS. 2A-2C are magnified, cross-sectional views of a coupling surface 218 in relation to a support structure 214, an ultrasound sensor 220, and a material layer 222, according to aspects of the present disclosure.

In FIG. 2A, the first shaded region 224 depicts a portion of the external surface 216 onto which a portion of the material layer 222 is disposed. The second shaded region 226 depicts a portion of the material layer 122 disposed between the coupling surface 218 and an acoustic backing material 230. The material layer 222 in the second shaded region 226 provides a heat transmission path between the coupling surface 218 and the external surface 216, such that when the ultrasound sensor 220 is coupled to the support structure 214 at the coupling surface 218 and is in direct contact with the material layer 222 in the second shaded region 226, heat from the ultrasound sensor 220 is transmitted away to the support structure 214 via the heat transmission path of the material layer 222.

The ultrasound sensor 220 comprises an acoustic stack 228 and an acoustic backing material 230. The backing material 230 may be used to attenuate or absorb acoustic energy not directed to the anatomy of interest. The backing material 230 may be disposed adjacent to and/or in contact with the acoustic stack 228, and may be coupled to the acoustic stack 228 using any suitable coupling, such as those described with respect to FIG. 1. While FIG. 2A shows the dimensions of the backing material 230 and the acoustic stack 228 to be the same, they may also be different. While FIG. 2A illustrates that the backing material 230 is positioned proximally of the acoustic stack 228, it is understood that the backing material 230 may have any suitable geometry within the ultrasound sensor 220, including on the sides of the acoustic stack 228. The backing material 230 may be made of any suitable material, including polymers, composites, ceramics, metals, or any combination thereof. The acoustic stack 228 may include a number of acoustic elements, such as piezoelectric elements, arranged in layers. For example, the one or more layers of the acoustic stack may be arranged on top of one another in a pillar form. Further, the acoustic stack may be divided into a plurality of acoustic elements. These elements may be arranged in a one-dimensional, a 1.x-dimensional, or two-dimensional array. The array may be of any type, i.e., linear, curved, annular, and the excitation of the elements may be simultaneous, in sequence, in phase, etc.

FIG. 2B shows a magnified, cross-sectional view similar to that of FIG. 2A, except that the ultrasound sensor 220 comprises a heat- or thermally-conductive structure 232 in addition to an acoustic backing material 230 and an acoustic stack 228. While FIG. 2B shows that the dimensions of the components of the ultrasound sensor 220 are the same, they may also be dimensionally different and may be arranged differently than illustrated. The thermally-conductive structure 232 may be used to increase the thermal conductivity of the ultrasound sensor 220, and may be comprised of any thermally-conductive material as earlier described with respect to FIG. 1.

In some examples, the thermally-conductive structure 232 may be disposed adjacent and proximal to the backing material 230. It is understood that the thermally-conductive structure 232 and/or backing material 230 may have any suitable geometry within the ultrasound sensor 220, including on the sides of the acoustic stack 228. The thermally-conductive structure 232 may be coupled to the backing material 230 by any of the coupling techniques described with respect to FIG. 1. Thus, a heat transmission path may be provided from the acoustic stack 228 to the backing material 230 and to the thermally conductive structure 232. The heat transmission path may be further extended to include a support structure 214. For example, the acoustic stack 228 may be coupled to the support structure 214 at a coupling surface 218, and the coupling surface 218 may be disposed with a material layer 222 (e.g., at shaded region 226). Further, the material layer 222 may extend from the coupling surface 218 to include an external surface 216 (e.g. at shaded region 224). Thus, the heat transmission path may be extended from the thermally conductive structure 232 to the support structure 214 via the material layer 222, and heat may thereby be transmitted away from the ultrasound sensor 220 to the support structure 214.

FIG. 2C shows a magnified, cross-sectional view similar to those of FIGS. 2A and 2B, except that ultrasound sensor 220 comprises a material layer 234 in addition to the thermally-conductive structure 232, acoustic backing material 230 and acoustic stack 228 of FIG. 2B. The material layer 234 may be used to further increase the thermal conductivity of the ultrasound sensor 220, and may be comprised of graphite, pyrolytic graphite, or of any thermally-conductive material such as those earlier described with respect to FIG. 1.

In some examples, the material layer 234 may be disposed adjacent and proximal to the thermally-conductive structure 232. It is understood that the material layer 234, the thermally-conductive structure 232, and/or backing material 230 may have any suitable geometry within the ultrasound sensor 220, including on the sides of the acoustic stack 228. The material layer 234 may be coupled to the thermally-conductive structure 232 by any of the coupling techniques described with respect to FIG. 1. Thus, a heat transmission path may be provided from the acoustic stack 228 to the backing material 230, then to the thermally conductive structure 232, and then to the material layer 234. The heat transmission path may be further extended to include a support structure 214. For example, acoustic stack 228 may be coupled to the support structure 214 at a coupling surface 218, and the coupling surface 218 may be disposed with a continuous material layer 222 (e.g., at shaded region 226). Further, the material layer 222 may extend from the coupling surface 218 to include an external surface 216 (e.g. at shaded region 224). Thus, the heat transmission path may be extended from the material layer 234 to the support structure 214 via the continuous material layer 222, thereby transmitting heat away from the ultrasound sensor 220 to the support structure 214.

FIGS. 3A-3F are exemplary illustrations and photographs of the support structure 314 in relation to the material layers 324 and 326 disposed on various surfaces, according to aspects of the present disclosure. The material in the material layers 324 and 326 may be one or more of the thermally conductive materials described earlier.

FIG. 3A is an exemplary illustration of the support structure 314 with external surfaces 316 and coupling surfaces 318 according to aspects of the present disclosure. In FIG. 3A, a material layer 326 has been continuously disposed on two of the four coupling surfaces 318 visible from the perspective of FIG. 3A, such that when an ultrasound sensor 320 is coupled to the support structure 314, the ultrasound sensor 320 would contact the support structure 314 at the material layer 326.

FIG. 3B is an exemplary illustration of the support structure with external surfaces and coupling surfaces according to aspects of the present disclosure. Unlike FIG. 3A, the coupling surfaces 318 in FIG. 3B are not disposed with a material layer. Instead, the external surfaces of the support structure, i.e., the support structure's proximal end (the end coupled to a ferrule), body (the rectilinear middle portion), and distal end (the end coupled to the ultrasound sensor) are continuously disposed with a material layer 324. As FIG. 3B suggests, the body may be completely, or almost completely covered by the material layer, and the material layer may be further disposed on other parts of the support structure. For example, the material layer may be disposed on an external surface of a distal protrusion of the support structure, as shown by portion 328 of the material layer. As another example, the material layer may also be disposed on an external surface of the proximal portion of the support structure, as shown by portion 330 of the material layer.

FIG. 3C is an exemplary illustration of the support structure with a material layer disposed continuously on both its external surfaces and coupling surfaces. The externally-disposed material layer 324, which is disposed on the external surfaces of the support structure, may be continuous with the coupling surface-disposed material layer 326 disposed on the coupling surfaces of the support structure. (See e.g., coupling surfaces 318 of FIG. 3A.) While FIG. 3C shows only a few surfaces of the body of the support structure disposed with the material layer, more or less of the external and coupling surfaces of the support structure may be disposed with the material layer. This includes disposing additional surfaces at the proximal portion of the support structure with material layer. One or more material layers may be implemented with the support structure to active a stable operating temperature. For example, the stable operating temperature may be below 43 degrees Celsius.

FIG. 3D is an exemplary photograph of a support structure 314 with a material layer (in this case, graphite) disposed on portions of its external surfaces and coupling surfaces, forming externally-disposed material layer 324 and coupling surface-disposed material layer 326 disposed on coupling surfaces (see e.g., coupling surfaces 318 of FIG. 3A). Material layers 324 and 326 may be continuous, e.g., cut or formed from a single continuous layer or joined from multiple layers without substantial discontinuity so as to significantly impair the thermal performance of the layers. Alternatively or additionally, the size, shape, form, thickness and other mechanical properties of the material layers 324 and 326 may be optimized to meet the required stable operating temperature while minimizing the amount of material used. Thus, the material layers 324 and 326 may, for example, include cut-outs or be in the form of continuous or discontinuous strips. Even with cut-outs or discontinuities in the material layers 324 and 326, the material layers 324 and 326 may still continuously join the heat-generation components (heat sources) with the non-heat generating components (heat sinks) to create a continuous heat path, such that when the ultrasound sensor is coupled to the support structure at the coupling surfaces and placed in contact with the material layer disposed on the coupling surfaces, heat from the ultrasound sensor may be transmitted to the coupling surfaces and to the external surfaces of the support structure by the material layers 324 and 326.

Figure 3E:
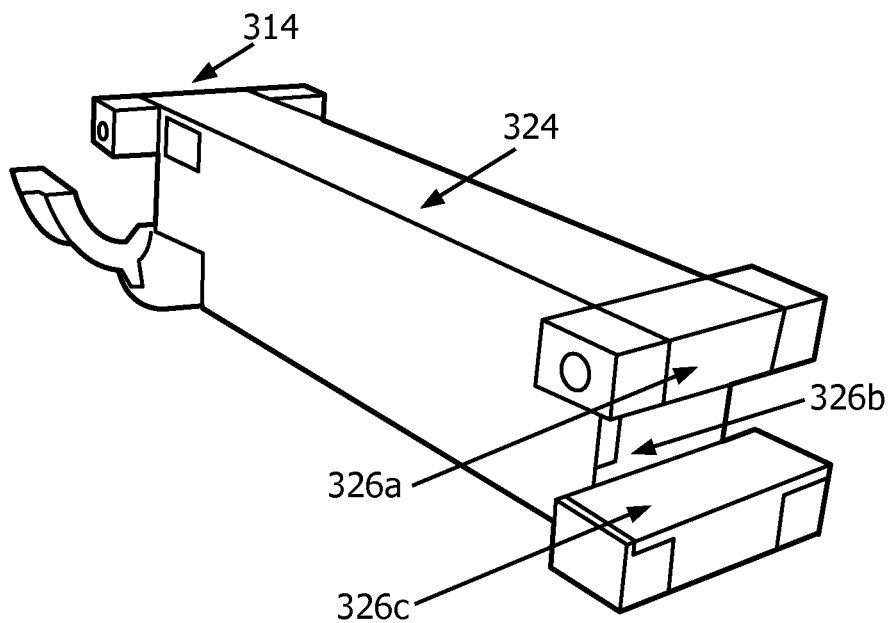
FIG. 3E is another exemplary photograph of a support structure in relation to a material layer disposed on various surfaces of the support structure, according to aspects of the present disclosure.

FIG. 3E is an exemplary photograph of a support structure 314 with a material layer (in this case, graphite) disposed on portions of its external surfaces and coupling surfaces, forming externally-disposed material layer 324 and coupling surface-disposed material layer 326a, 326b, and 326c disposed on the coupling surfaces (see e.g., coupling surfaces 318 of FIG. 3A). In some examples, coupling surface-disposed material layer 326a, 326b, and 326c may not be made from a single layer, especially if the coupling surface geometry is complex. Even if made from overlapping layers, the layers may overlap to provide a continuous heat path. The heat path may be optimized, for example using different shapes, geometries, cut-outs, etc., to meet the target stable operating temperature. In other examples, such shown as shown in FIG. 3E, the coupling surface-disposed material layer may be made from a single material layer. As shown in FIG. 3E, coupling surface-disposed material layer 326a, 326b, and 326c may be respectively disposed on an outer top portion, an inner bottom portion, and an inner side portion of the coupling surface.

Figure 3F:
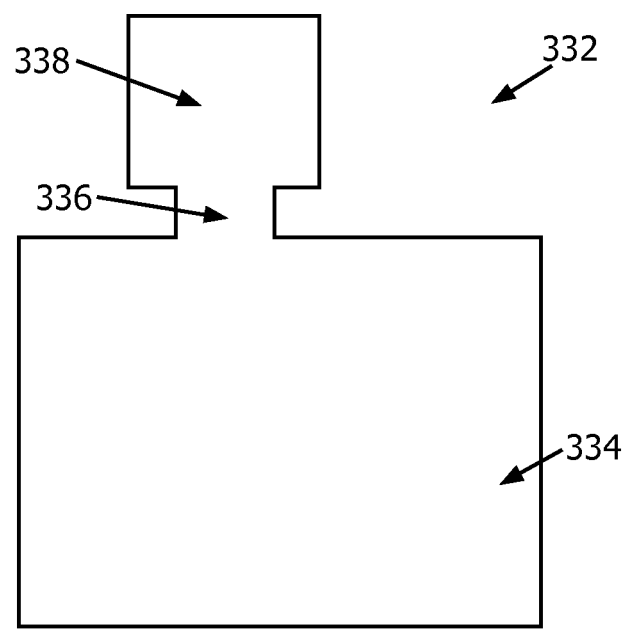
FIG. 3F is an exemplary illustration of a material layer.

FIG. 3F is an exemplary illustration of a single, continuous material layer 332 disposable (and before it is disposed) on the external surfaces and coupling surfaces of a support structure 314. The material layer 332 may be cut, shaped, formed, assembled, or otherwise made to optimally conform to the shape of the support structure 314. For example, the material layer 332 may include a body portion 334, a neck portion 336, and a head portion 338. In some examples, the body portion 334 of the material layer 332 may be disposed over the body of the support structure 314, forming externally-disposed material layer 324 of FIG. 3E. In some examples, the neck portion 336 of the material layer 332 may be disposed over the inner bottom portion of the coupling surface, forming coupling surface-disposed material layer 326b. In some examples, the head portion 338 of the material layer 332 may be disposed over the inner side portion of the coupling surface, forming coupling surface-disposed material layer 326c. In some examples, the head portion 338 of the material layer 332 may be disposed over the outer top portion of the coupling surface, forming coupling surface-disposed material layer 326a. Other combinations are possible. For example, depending on the form of the support structure 314, other features such as "arms" may be fashioned from the material layer 332 for disposing over corresponding features of the support structure 314.

Figure 4:
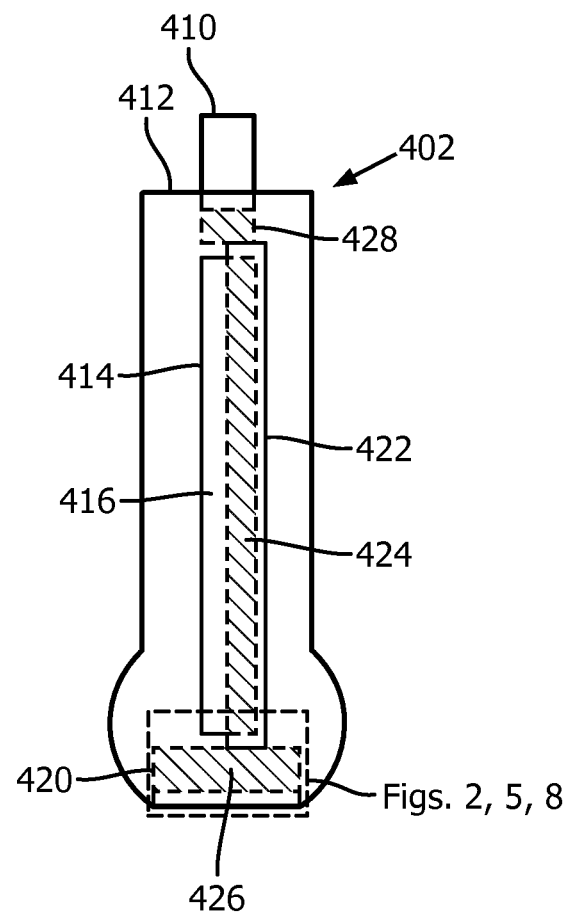
FIG. 4 is a diagrammatic schematic view of an ultrasound imaging system, according to aspects of the present disclosure.

FIG. 4 is a diagrammatic schematic view of an ultrasound imaging probe 402, according to aspects of the present disclosure. The imaging probe 402 of FIG. 4 differs from the imaging probe 102 of FIG. 1 in that the material layer 422 is disposed on external surfaces of the support structure 414, the ultrasound sensor 420, and the ferrule 410. The material layer 422 may be further disposed on the coupling surface of the support structure 414, as shown in FIG. 8. The material layer 422 may be made of one or more thermally conductive materials, such as those described with respect to FIG. 1.

Like the imaging probe 102 of FIG. 1, the imaging probe 402 is comprised of a ferrule 410, a housing 412, a support structure 414, an ultrasound sensor 420, and a material layer 422. The material layer 422 is disposed on various surfaces of the imaging probe 402, including an external surface of the support structure 414 (as depicted by the first shaded region 424), an external surface of the ultrasound sensor 420 (as depicted by the second shaded region 426), and an external surface of the ferrule 410 (as depicted by the third shaded region 428).

Thus disposed, the material layer 422 provides a heat transmission path from the ultrasound sensor 420 to the support structure 414. For example, heat may be first transmitted from the ultrasound sensor 420 to the externally-disposed material layer of the ultrasound sensor at shaded region 426, then to the externally-disposed material layer at shaded region 424 of the support structure 414, and then to the externally-disposed material layer at shaded region 428 of the ferrule 410. Heat may further be transmitted from the material layer to the support structure 414 and the ferrule 410 by the material layer disposed on those surfaces, i.e., at shaded regions 424 and 428 respectively. The support structure 414 and the ferrule 410 may act as heat sinks. Because the material layer 422 may be continuous along this heat transmission path, the material layer 422 may be more efficient at transmitting heat than if it were non-continuous. Additionally, the microstructure of the material layer 422 may be aligned, oriented, or otherwise designed to maximize thermal conductivity.

As illustrated in FIGS. 2, 5, and 8, the ultrasound sensor 420 may comprise several elements, such as an acoustic stack, an acoustic backing layer, a thermally-conductive structure, and a material layer.

Figure 5A:
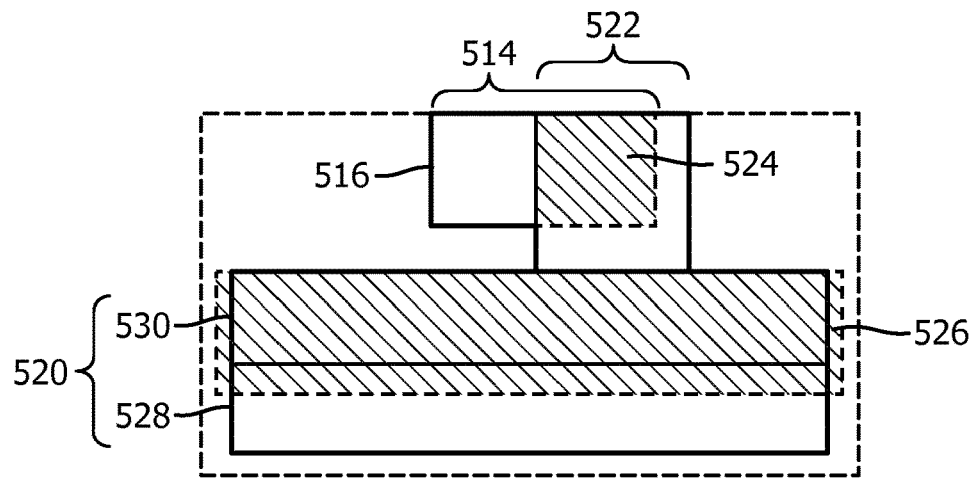
FIG. 5A is an exemplary cross-sectional view of an ultrasound sensor in relation to a support structure and a material layer, according to aspects of the present disclosure.
Figure 5B:
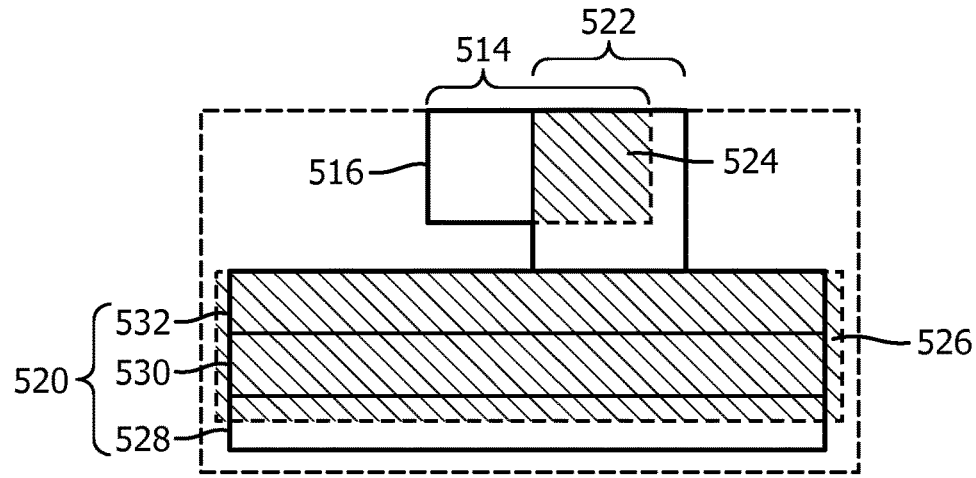
FIG. 5B is another exemplary cross-sectional view of an ultrasound sensor in relation to a support structure and a material layer, according to aspects of the present disclosure.
Figure 5C:
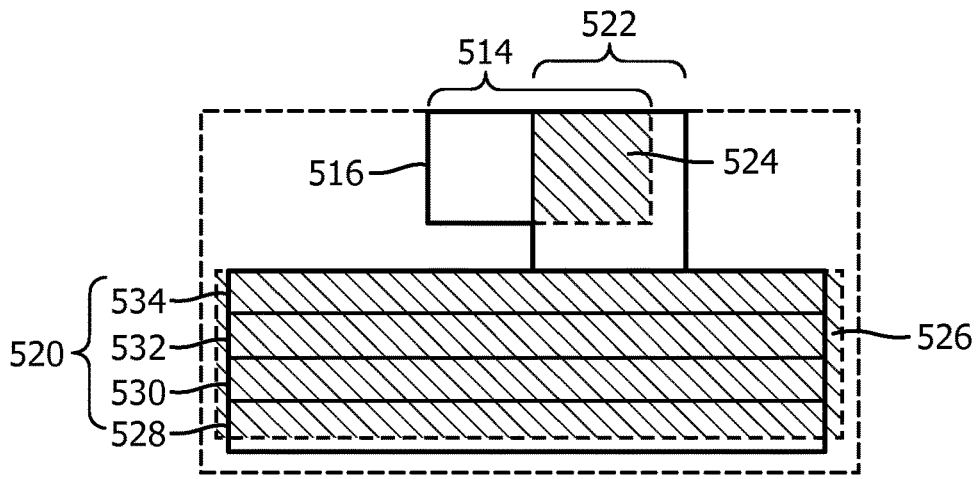
FIG. 5C is a further exemplary cross-sectional view of an ultrasound sensor in relation to a support structure and a material layer, according to aspects of the present disclosure.

FIGS. 5A-5C are magnified, cross-sectional views of an ultrasound sensor 520 in relation to a support structure 514 and a material layer 522. The material layer 522 may be comprised of two portions, a first portion and a second portion, and the first portion may be contiguous, continuous, and/or unbroken with the second portion. The material layer 522 may be made of one or more thermally-conductive materials, such as those described with respect to FIG. 1.

In FIG. 5A, the first portion 526 of the material layer 522 may be disposed over an ultrasound sensor 520, and the second portion 524 of the material layer 522 may be disposed over an external surface 516 of the support structure 514. As illustrated in FIG. 5A, the material layer 522 may be fully disposed over an external surface of an acoustic backing material 530 and partially disposed over an external surface of an acoustic stack 528. In some examples, the material layer 522 is fully disposed over one or both external surfaces, while in other examples, the material layer 522 is partly disposed over one or both external surfaces.

Returning to the example in FIG. 5A, heat may be transmitted from the external surfaces of the acoustic stack 528 and the acoustic backing material 530 to the first portion 526 of the material layer 522 disposed over those surfaces, then to the material layer 522 at the second portion 524 disposed over the external surface 516 of the support structure 514, and then to the support structure 514. As described with respect to FIG. 4, the heat may be further transmitted by the material layer 522 from the support structure 514 to the ferrule 410.

FIG. 5B shows a magnified, cross-sectional view similar to that of FIG. 5A, except that here the ultrasound sensor 520 comprises a thermally-conductive structure 532 in addition to an acoustic backing material 530 and an acoustic stack 528. The geometry, dimensions, and placement of each of the components of the ultrasound sensor 520 may vary. The thermally-conductive structure 532 may be used to increase the thermal conductivity of the ultrasound sensor 520, and may be comprised of any thermally-conductive material, such as those described with respect to FIG. 1.

As illustrated in FIG. 5B, the material layer 522 is disposed over all of an external surface of the thermally-conductive structure 532, over all of an external surface of the acoustic backing material 530, and over a portion of an external surface of an acoustic stack 528. In some examples, the material layer 522 may also be disposed over all, some, or none of each of the external surfaces of each of the acoustic stack 528, backing material 530, and/or thermally-conductive structure 532. As disposed in FIG. 5B, the material layer 522 may transmit heat from the ultrasound sensor 520 to the support structure 514 via a first portion 526 of the material layer 522 disposed over the acoustic stack 528, the backing material 530, and the thermally-conductive structure 532, the heat transmission path continuing via a second portion 524 of the material layer 522 disposed over an external surface 516 of the support structure 514. As described with respect to FIG. 4, the heat transmission path may be further extended, and the heat further transmitted, by the material layer 522 extending from the support structure 514 to the ferrule 410.

FIG. 5C shows a magnified, cross-sectional view similar to those of FIGS. 5A and 5B, except that ultrasound sensor 520 further comprises a material layer 534 in addition to the thermally-conductive structure 532, acoustic backing material 530 and acoustic stack 528 of FIG. 5B. The geometry, dimensions, and placement of each of the elements of the ultrasound sensor 520 may vary. The material layer 534 may be used to further increase the thermal conductivity of the ultrasound sensor 520, and may be comprised of graphite, pyrolytic graphite, or any thermally-conductive material such as those described with respect to FIG. 1.

As illustrated in FIG. 5C, the material layer 522 is disposed over all of an external surface of the material layer 534, all of an external surface of the thermally-conductive structure 532, all of an external surface of the acoustic backing material 530, and over a portion of an external surface of an acoustic stack 528. However, the material layer 522 may also be disposed over all, some, or none of each of the external surfaces of each of the acoustic stack 528, backing material 530, thermally-conductive structure 532 and/or material layer 534. As disposed in FIG. 5B, the material layer 522 may transmit heat from the ultrasound sensor 520 to the support structure 514 via a first portion 526 of the material layer 522 disposed over the acoustic stack 528, the backing material 530, the thermally-conductive structure 532, and the material layer 534, the heat transmission path continuing via a second portion 524 of the material layer 522 disposed over an external surface 516 of the support structure 514. As described with respect to FIG. 4, the heat transmission path may be further extended, and the heat further transmitted, by the material layer 522 extending from the support structure 514 to the ferrule 410.

FIGS. 6A-6D are exemplary illustrations and a photograph of the support structure 614 in relation to the material layer 624, 626, and 628 disposed on the external surfaces of the support structure 614, ultrasound sensor 620, and ferrule 610 respectively. The material layers 624, 626, and 628 may be contiguous or continuous with one another, in some instances. Thus, 624, 626, 628 may identify different portions of single, whole material layer, rather than three different material layers. Material layers 624, 626, and 628 may be comprised of more than one material layer joined together in some instances. The material layers 624, 626, and 628 may be made of one or more thermally conductive materials, such as those described with respect to FIG. 1.

Figure 6A:
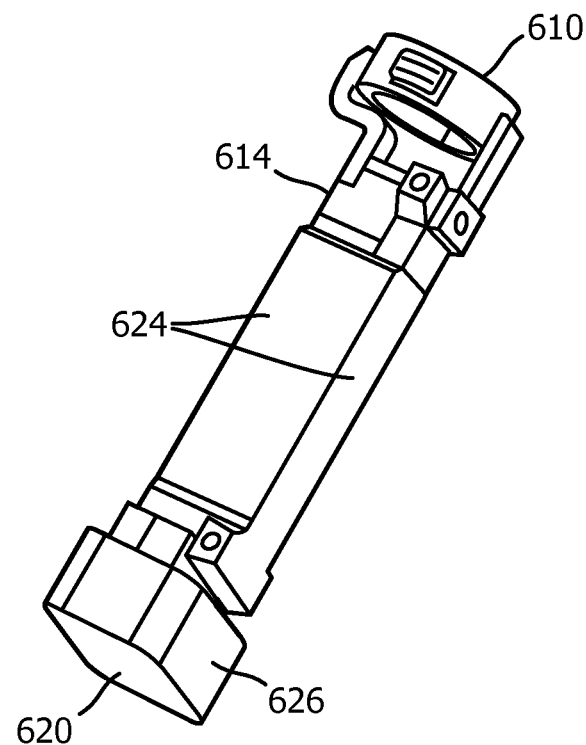
FIG. 6A is an exemplary illustration of a support structure in relation to a material layer disposed on various surfaces of the support structure, according to aspects of the present disclosure.

FIG. 6A is an illustration of a support structure 614 with a ferrule 610 at a proximal portion of the support structure 614 and an ultrasound sensor 620 at a distal portion of the support structure 614. The external surfaces of a body of the support structure 614 and the external surfaces of the ultrasound sensor 620 are shown disposed with material layers. The material layer 624 disposed over the support structure 614 may be continuous with the material layer 626 disposed over the ultrasound sensor 620, and the ultrasound sensor 620 may include features shown in FIGS. 2, 5 and 8. In FIG. 6A, the ferrule 610 has not been disposed with a material layer.

Figure 6B:
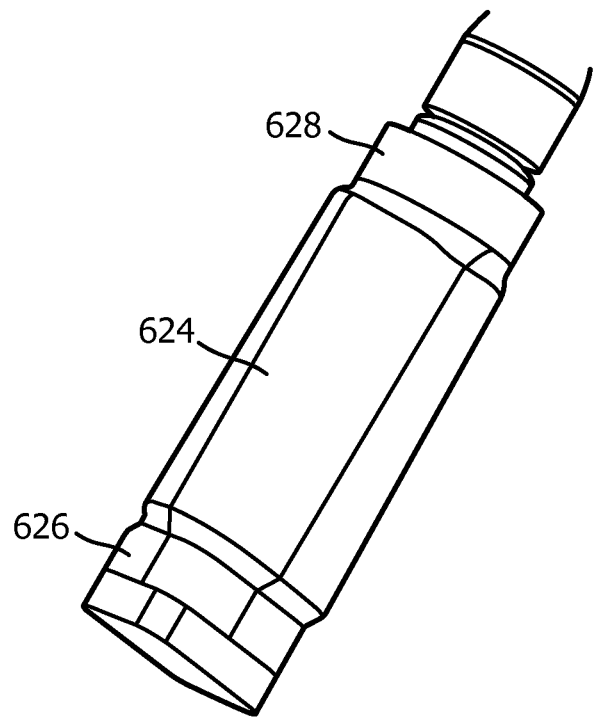
FIG. 6B is another exemplary illustration of a support structure in relation to a material layer disposed on various surfaces of the support structure, according to aspects of the present disclosure.

FIG. 6B is an illustration of a support structure wherein the external surfaces of the ultrasound sensor 620, the support structure 614, and the ferrule 610 of FIG. 6A have all been disposed with a material layer. The material layer 626 disposed on the external surface of the ultrasound sensor 620 may be continuous with the material layer 624 disposed on the external surface of the support structure 614 and with the material layer 628 disposed on the external surface of the ferrule 610. The material layers 624, 626, and 628 may be dimensioned such that each of the material layers are respectively contained or disposed within a housing when the housing is assembled and closed.

Figure 6C:
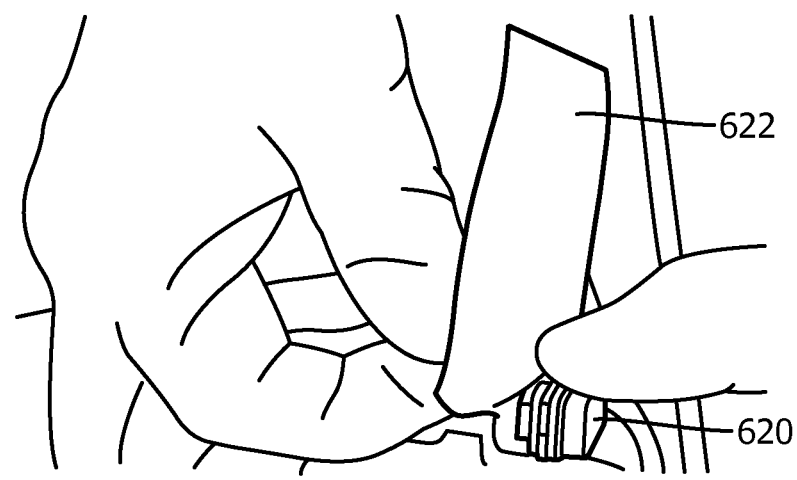
FIG. 6C is an exemplary photograph of a support structure in relation to a material layer disposed on various surfaces of the support structure, according to aspects of the present disclosure.

FIG. 6C is an exemplary photograph of a material layer 622 (in this case, graphite) being disposed onto the external surface of the ultrasound sensor 620, support structure, 614 and ferrule 610 of FIG. 6A. Here, the material layer 622 is in the form of an adhesive film, and a user has begun to adhere the material layer 622 onto the ultrasound sensor 620, such as may be performed during an assembly process of an ultrasound imaging probe 102.

Figure 6D:
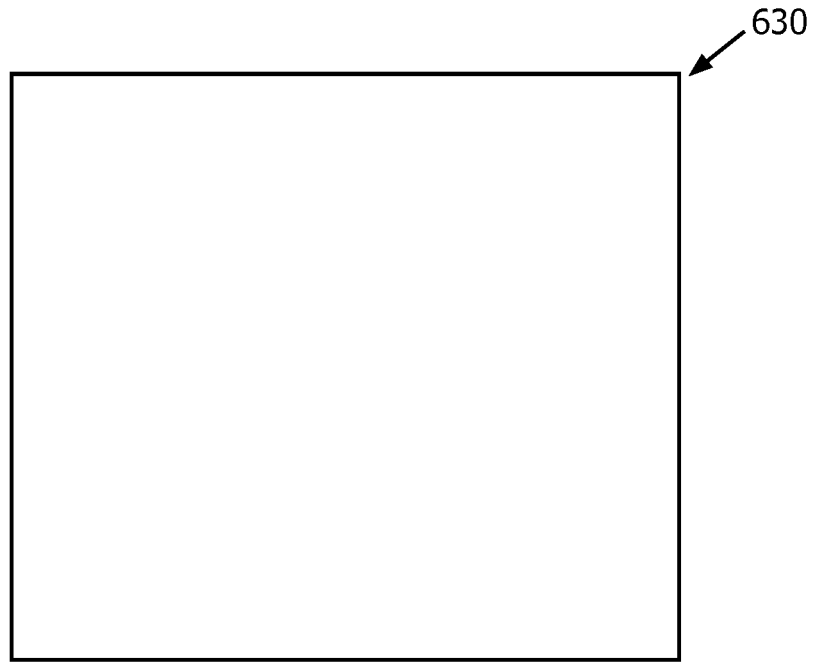
FIG. 6D is an exemplary illustration of a material layer.

FIG. 6D is an exemplary illustration of a material layer 630 disposable (and before it is disposed) on external surfaces of the ultrasound sensor 620, the support structure 614, and the ferrule 610 of FIG. 6A. The material layer 630 may be cut, shaped, formed, assembled, or otherwise made to optimally conform with the shape of the ultrasound sensor 620, the support structure 614, and the ferrule 610. For example, the material layer 630 may be shaped like a square or rectangle, as shown. The material layer 630 may also be shaped in any other regular or irregular shape, be rectilinear or curved, or be some combination of the abovementioned forms. In some examples, the material layer 630 may be a compliant fabric, a gel, a polymer, or other material capable of draping over and taking the shape of one or more of the ultrasound sensor 620, the support structure 614, and/or the ferrule 610. The material layer 630 may be made of one or more thermally conductive materials, such as those described with respect to FIG. 1.

Figure 7:
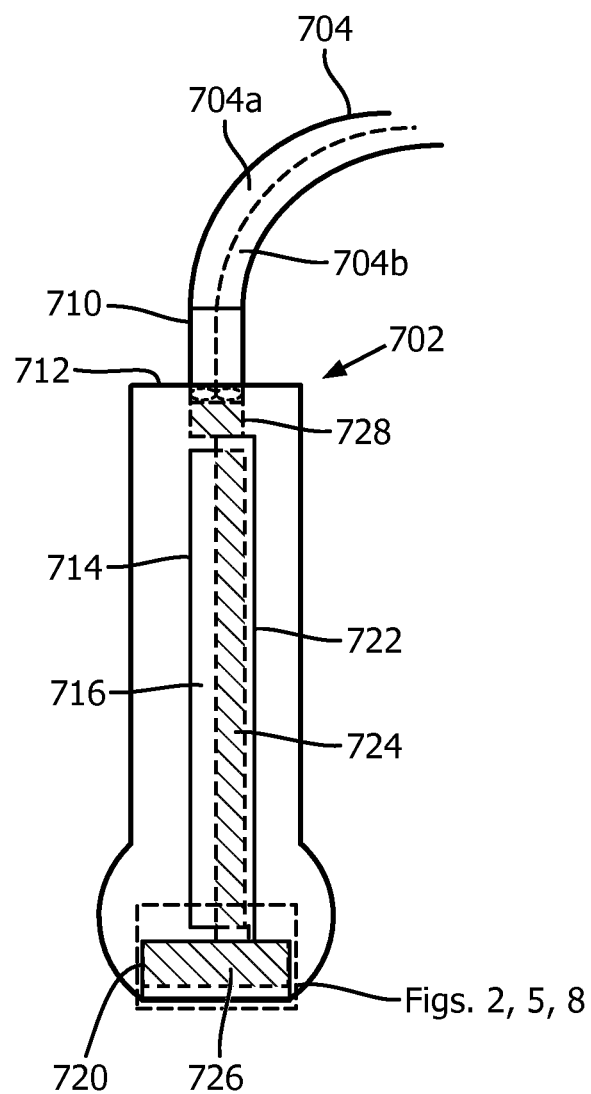
FIG. 7 is a diagrammatic schematic view of an ultrasound imaging system, according to aspects of the present disclosure.

FIG. 7 is a diagrammatic schematic view of an ultrasound imaging probe 702. The elements of the imaging probe 702 are essentially the same as those of imaging probe 402, and for the sake of brevity will not be described here in detail. Briefly, the imaging probe 702 comprises a ferrule 710, a housing 712, a support structure 714, an external surface 716, an ultrasound sensor 720, and a material layer 722. The material layer 722 may be formed from a single material layer, or may be formed from multiple layers joined together. For example, portions 724, 726, and 728 of the material layer 722 may be individual pieces of a material layer joined together, or may be convenient references to different portions of a single, whole material layer. The portions 724, 726 and 728 of the material layer 722 may be continuously disposed on the external surface 716 of the support structure 714, on an external surface of the ultrasound sensor 720, and on an external surface of the ferrule 710.

FIG. 7 additionally shows a communication cable 704 with communication cable elements 704a and 704b disposed within the communication cable 704. While two communications elements 704a and 704b are shown, communications cable 704 may comprise more or less communications elements. In some examples, the communications elements 704a and 704b terminate at an inner portion of the ferrule 710 within the housing 712. However, in other examples, the communications elements may terminate at an outer portion of the ferrule 710 outside the housing 712.

The cable elements may be braided and insulated, and in addition, the ferrule 710 may be provided at the cable junction to protect the cable 704 from mechanical stresses. FIG. 7 shows that a portion of the ferrule 710 is disposed within the housing 712, with a remaining portion disposed outside of the housing 712. In some examples, the ferrule 710 is disposed entirely within or outside of the housing 712. The internally-disposed portion of the ferrule 710 may be coupled to a support structure 714, while the externally-disposed portion may be coupled to the housing 712.

In some examples, an external surface of the cable 704 or of the cable elements 704a and 704b disposed within the housing 712 is in direct contact with an internal surface of the ferrule 710. Externally, the ferrule 710 may be disposed with a portion 728 of a material layer 722. The ferrule 710 and the material layer 722 may be made up of one or more thermally conductive materials, such as those described with respect to FIG. 1. Thus, the heat transmission path described with respect to FIG. 4 may be further extended from the external surface of the ferrule 710 to its internal surface by virtue of the ferrule's thermal conductivity, and from the ferrule's internal surface to the communication cable elements (e.g., 704a and 704b), and/or the communication cable 704, and/or their braiding (which may itself be thermally-conductive) by virtue of their respective thermal conductivities. To further enhance heat transmission, the communications cable 704, communication cable elements 704a and 70b, and/or their braiding, may be externally disposed or wrapped with the same material as material layer 722.

The cable elements 704a and 704b may terminate in a plug or connector within the housing at its proximal end. The plug or connector may be coupled with a receptacle or slot of one or more printed circuit boards. The one or more printed circuit boards themselves may be coupled to the support structure 714 at proximal and distal ends of the support structure by, for example, screws. The printed circuit board may include a processor and a memory described with respect to FIG. 1, and the dimensions of the support structure 714 may be designed to suit the dimensions of the printed circuit board (or vice versa).

A flat, flexible cable may be used to connect the ultrasound sensor 720 at the distal end of the support structure 714 to a receptacle or slot of the one or more printed circuit boards. The flexible cable may be used to transmit power, data and computer processing instructions between the ultrasound sensor 720 and the processor and memory coupled to the one or more printed circuit boards. Power, data, and instructions may further be transmitted between the imaging probe 702 and the processing system described with respect to FIG. 1 by the communication cable 704. In some examples, data from the flexible cable may further be transmitted up and down the communication cable via buses of the one or more printed circuit boards. In some examples, the flexible cable may provide a direct route for power and data to flow between the ultrasound sensor 720 and the communication cable via a wire-to-wire interface such as a male-to-female connector.

In some examples, imaging probe 702 includes a thermal interface material (TIM) or thermal gap filler pad. The TIM or thermal gap filler pad may be used to provide a heat conduction path from the support structure to the housing, and may be dimensioned such that the TIM contacts the housing when the imaging probe 702 is assembled. In some examples, the TIM may be disposed on a surface of the support structure 714. However, the placement of the TIM may vary depending on the design of the support structure 714 and of the housing of the imaging probe 702.

The TIM or thermal gap filler pad may be comprised of a compliant or compressible thermally-conductive material, such as a silicone polymer combined with a ceramic thermal medium. The compliance or compressibility of the TIM or thermal gap filler pad increases the effective thermal conductivity of the TIM or thermal gap filler pad by reducing the presence of air pockets between the TIM or thermal gap filler pad and the housing. Other types of TIM, such as thermal pastes, liquid thermal compounds, etc., may also be used. Generally, the physical form (i.e., pad, paste, liquid, etc.) of TIM used depends on the contact surface and the amount of space to be bridged by the TIM. Pads may be more suitable for taller spaces.

Figure 8A:
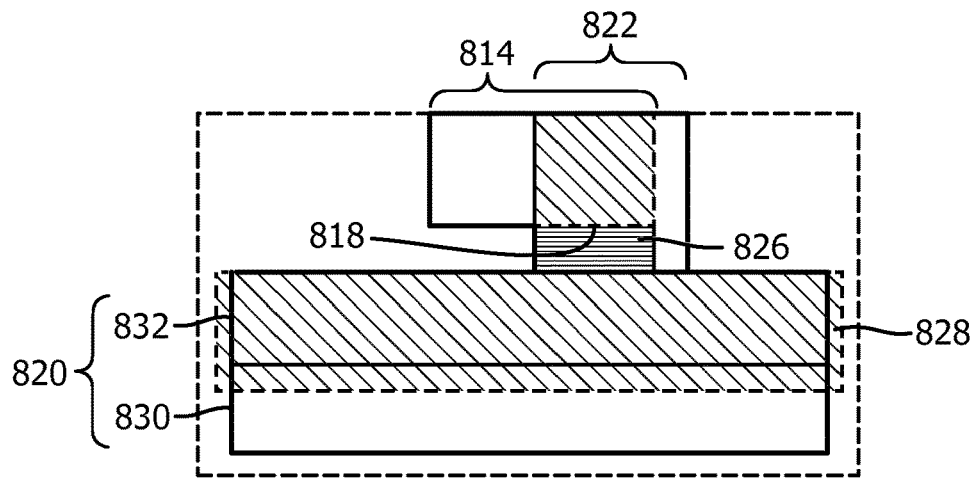
FIG. 8A is an exemplary cross-sectional view of a coupling surface and an ultrasound sensor in relation to a support structure and a material layer, according to aspects of the present disclosure.
Figure 8B:
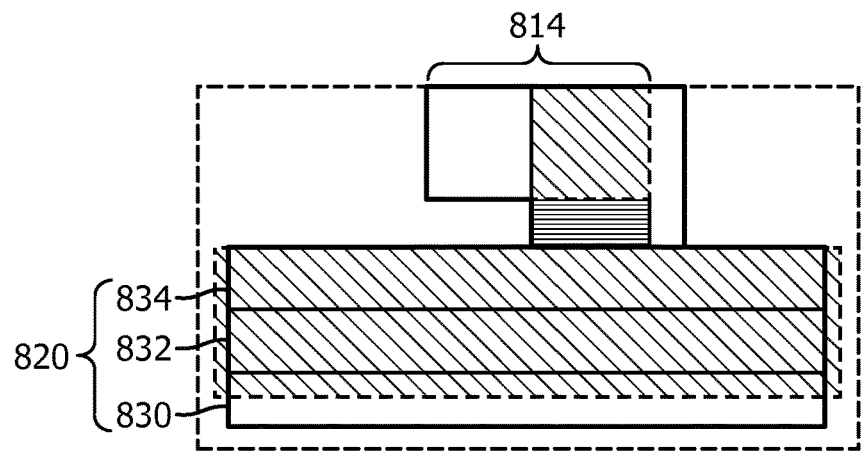
FIG. 8B is an exemplary cross-sectional view of a coupling surface and an ultrasound sensor in relation to a support structure and a material layer, according to aspects of the present disclosure.
Figure 8C:
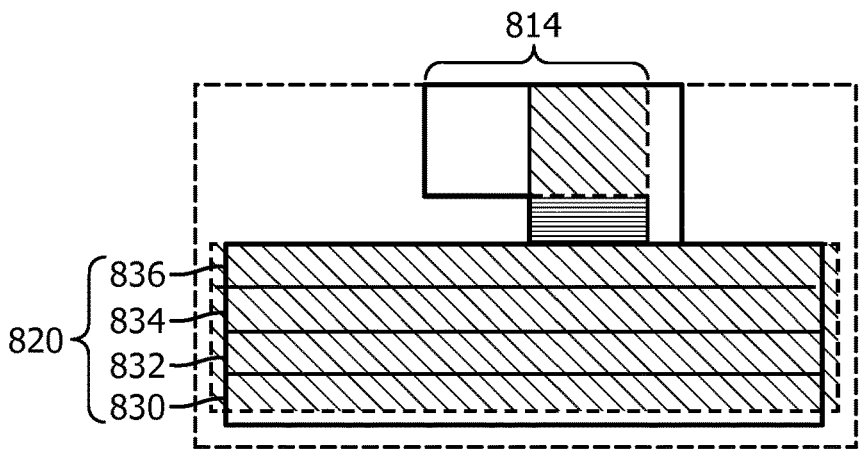
FIG. 8C is an exemplary cross-sectional view of a coupling surface and an ultrasound sensor in relation to a support structure and a material layer, according to aspects of the present disclosure.

FIGS. 8A-8C are magnified, cross-sectional views of a coupling surface 818 and an ultrasound sensor 820 in relation to a support structure 814 and a material layer 822. FIGS. 8A-8C show a combination of the features of FIGS. 2A-2C and FIGS. 5A-5C. Specifically, in FIGS. 8A-8C, the material layer 822 is contiguously or continuously disposed over both the coupling surface 818 (see FIGS. 2A-2C) and the external surface of the ultrasound sensor 820 (see FIGS. 5A-5C). The structures, including the material composition of the material layer 822, in FIGS. 8A-8C are substantially similar to those of FIGS. 2A-2C and FIGS. 5A-5C.

In FIGS. 8A-8C, a portion 826 of the material layer 822 is disposed on the coupling surface 818. More particularly, the portion 826 is disposed between, and in direct contact with, the support structure 814 and an acoustic backing material 832 (FIG. 8A), a thermally-conductive structure (FIG. 8B), and/or a material layer (FIG. 8C) of the ultrasound sensor 820. Thus, the portion 826 of the material layer 822 provides a first heat transmission path from the ultrasound sensor 820 to the support structure 814. This first heat transmission path is similar to the heat transmission path described in FIG. 2A.

A second heat transmission path similar to the one described with respect to FIGS. 5A-5C is also provided by the material layer 822 when the material layer 822 is disposed on an external surface of the ultrasound sensor 820. In FIG. 8A, the material layer 822 is disposed on external surfaces of an acoustic backing material 832 and an acoustic stack 830. In FIG. 8B, the material layer 822 is disposed on external surfaces of a thermally-conductive structure 834, an acoustic backing material 832, and an acoustic stack 830. In FIG. 8C, the material layer 822 is disposed on external surfaces of a material layer 836, a thermally-conductive structure 834, an acoustic backing material 832, and an acoustic stack 830. In each of FIGS. 8A-8C, the material layer 822 disposed on the various external surfaces of the ultrasound sensor 820 provide a heat transmission path to the external surfaces of the support structure 814 and beyond.

The combination of the first and second heat transmission paths in FIGS. 8A-8C may result in more efficient heat dissipation from the ultrasound sensor 820, thereby opening the door for more powerful and higher-resolution acoustic stacks or transducer arrays to be used.

Figure 9:
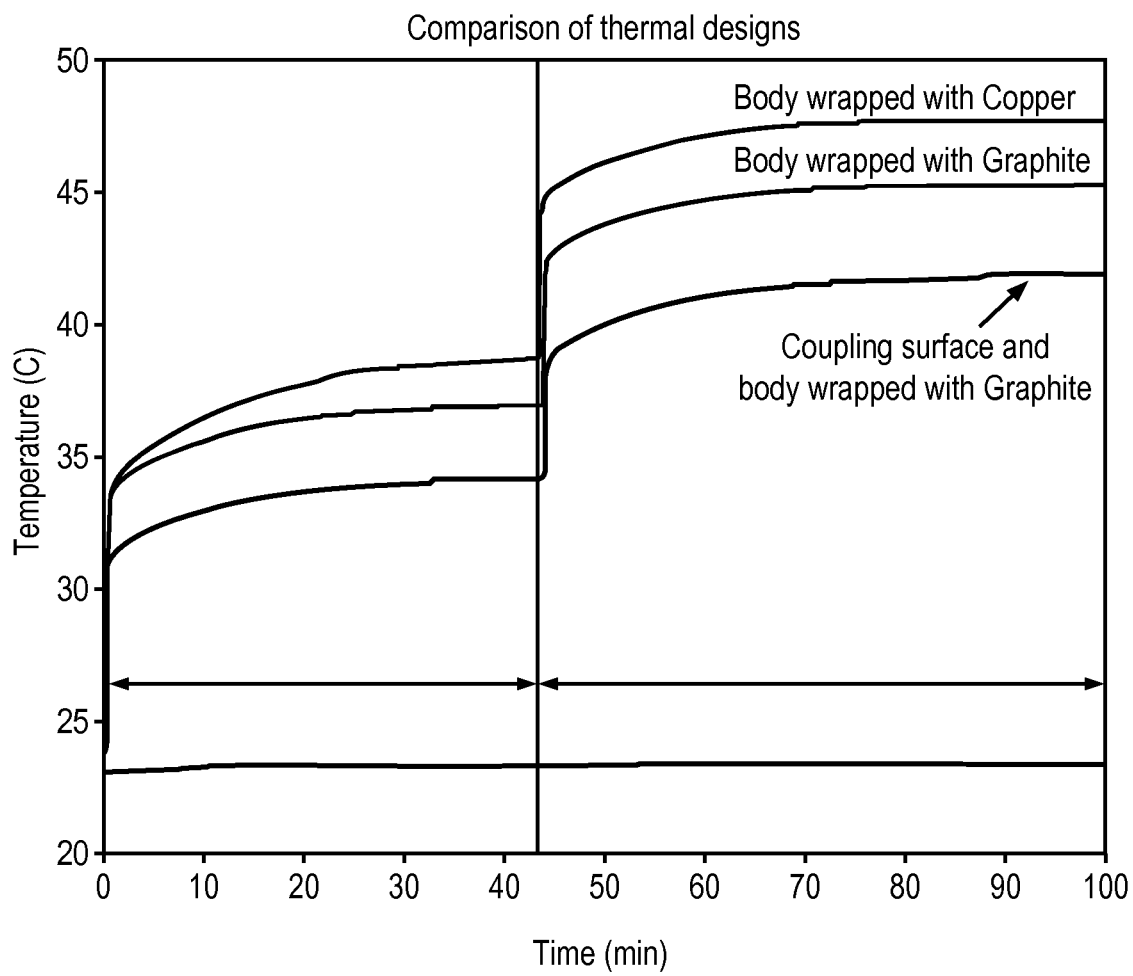
FIG. 9 is a temperature-time graph showing comparing various thermal designs for ultrasound imaging probes.

FIG. 9 is a temperature-time graph comparing three thermal designs for ultrasound imaging probes: 1) a probe with a copper-wrapped body; 2) a probe with a graphite-wrapped body; and 3) a probe with a graphite-wrapped body and a graphite-wrapped coupling surface. In this comparison, an ultrasound sensor was driven for approximately 40 minutes at low voltage and then for approximately an hour at high voltage. FIG. 10 shows that at the high voltage, the external surface temperature of the ultrasound sensor (the part of the ultrasound imaging probe normally in contact with a patient's skin) was approximately 8 degrees Celsius lower for the ultrasound imaging probe with the graphite-wrapped body and coupling surface as compared to the ultrasound imaging probe with only a copper-wrapped body. Even after an hour at high voltage, the probe with the graphite-wrapped body and coupling surface maintained an external surface temperature of below 43 degrees Celsius.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:
1. An ultrasound imaging probe, comprising:
  a housing configured for handheld use;
  a support structure different from the housing and disposed within the housing, the support structure comprising:
    a thermally-conductive material;

a coupling surface disposed at a distal portion of the support structure; and an outer surface different from the coupling surface;

a continuous thermally-conductive layer different from the thermally conductive material and coupled to the outer surface and the coupling surface of the support structure, the continuous thermally-conductive layer thereby providing a heat transmission path between the coupling surface and the outer surface; and an ultrasound sensor coupled to the support structure at the coupling surface and directly in contact with the continuous thermally-conductive layer at the coupling surface, such that heat from the ultrasound sensor is transmitted away to the support structure via the heat transmission path of the continuous thermally-conductive layer.

2. The probe of claim 1, wherein the coupling surface and the outer surface each comprise at least one planar surface of the support structure.

3. The probe of claim 1, wherein the ultrasound sensor comprises an acoustic stack and an acoustic backing material adjacent to the acoustic stack, wherein a surface of the ultrasound sensor that is directly in contact with the continuous thermally-conductive layer includes a surface of the acoustic backing material.

4. The probe of claim 1, wherein the ultrasound sensor comprises:

an acoustic stack;

an acoustic backing material adjacent to the acoustic stack; and a heat-conductive structure adjacent to the backing material, wherein a surface of the ultrasound sensor that is directly in contact with the continuous thermally-conductive layer includes a surface of the heat-conductive structure.

5. The probe of claim 1, wherein a second continuous thermally-conductive layer is disposed on an external surface of the ultrasound sensor, and wherein a surface of the ultrasound sensor that is directly in contact with the continuous thermally-conductive layer includes a surface of the second continuous thermally-conductive layer.

6. The probe of claim 1, wherein the support structure comprises a body and a protrusion extending from the body at the distal portion, wherein a surface of the protrusion comprises the coupling surface and a surface of the body comprises the outer surface.

7. The probe of claim 1, wherein the outer surface extends along a longitudinal axis of the support structure.

8. The probe of claim 1, wherein the continuous thermally-conductive layer comprises a graphite sheet bonded to an adhesive.

9. The probe of claim 1, further comprising a second continuous thermally-conductive layer disposed on one or more outer surfaces of the ultrasound sensor and the support structure, such that the second continuous thermally-conductive layer provides a second heat transmission path from the one or more outer surfaces of the ultrasound sensor to the one or more outer surfaces of the support structure, thereby also transmitting the heat away to the support structure.

10. The probe of claim 1, further comprising a ferrule and a second continuous thermally-conductive layer disposed on one or more outer surfaces of the ultrasound sensor, the support structure, and the ferrule, such that the second continuous thermally-conductive layer provides a second heat transmission path from the one or more outer surfaces of the ultrasound sensor to the one or more outer surfaces of the support structure and the ferrule, thereby also transmitting the heat away to the support structure and the ferrule.

11. The probe of claim 1, further comprising a ferrule, wherein the ferrule is disposed at a proximal portion of the support structure, wherein the continuous thermally-conductive layer is disposed on an outer surface of the ultrasound sensor and an outer surface of the ferrule such that the heat transmission path is from the ultrasound sensor to the support structure and the ferrule, and wherein the ultrasound sensor is directly in contact with the continuous thermally-conductive layer disposed on the outer surface of the ultrasound sensor, such that heat from the ultrasound sensor is transmitted away to the support structure and the ferrule via the heat transmission path of the continuous thermally-conductive layer.

12. The probe of claim 11, further comprising a communication cable disposed within the ferrule and in direct contact with an internal surface of the ferrule.

13. The probe of claim 12, wherein the communication cable is thermally coupled to the ferrule such that the heat is also transmitted away from the ultrasound sensor to the communication cable via the heat transmission path of the continuous thermally conductive layer.

14. The probe of claim 11, wherein the support structure comprises a body, and wherein the ferrule is coupled to the body at a proximal portion of the support structure.

15. The probe of claim 11, further comprising a second continuous thermally-conductive layer disposed on the coupling surface and the outer surface of the support structure, wherein the ultrasound sensor is coupled to the support structure at the coupling surface and directly in contact with the second continuous thermally-conductive layer, such that the second continuous thermally-conductive layer provides a second heat transmission path between the coupling surface and the external outer surface, thereby also transmitting the heat away to the support structure.

* * * * *